United States Patent [19]

Mosbach

[11] Patent Number: 5,110,833

[45] Date of Patent: May 5, 1992

[54] PREPARATION OF SYNTHETIC ENZYMES AND SYNTHETIC ANTIBODIES AND USE OF THE THUS PREPARED ENZYMES AND ANTIBODIES

[76] Inventor: Klaus Mosbach, Lackalänga 31-18, S-240 20 Furulund, Sweden

[21] Appl. No.: 500,892

[22] Filed: Mar. 29, 1990

[51] Int. Cl.$^5$ .............................. C08J 9/26; C08J 9/28
[52] U.S. Cl. ...................................... 521/50; 435/183; 435/188.5; 530/387.1; 530/388.1; 530/388.9; 530/389.8; 521/61; 521/64; 521/149; 521/150; 525/54.1
[58] Field of Search .................. 521/142, 149, 61, 64, 521/150; 525/54.1; 435/183; 530/387

[56] References Cited

U.S. PATENT DOCUMENTS 4,111,863 9/1978 Wulff et al. .
4,127,730 11/1978 Wulff et al. .

OTHER PUBLICATIONS

Shea et al, J. Am. Chem. Soc., 108, 1091–1093 (1986).
Tramontano et al, Science, vol. 234, 1566–1570 (1986).
Pollack et al, Science, vol. 234, 1570–1573 (1986).
Janda et al, Science, vol. 241, 1188–1191 (1988).
Andersson et al, Makromol. Chem., Rapid Commun., 10, 491–495 (1989).
Ekberg et al, Tibtech, vol. 7, 92–96 (1989).
Robinson et al, J. Chem. Soc., Chem. Commun., 969–970 (1989).

Primary Examiner—Morton Foelak
Attorney, Agent, or Firm—Birch, Stewart, Kolasch & Birch

[57] ABSTRACT

A method of preparing synthetic enzymes and synthetic antibodies in which method use is made of the so called molecular imprinting method, is described. As imprinting molecules use is made of transition state analogues, substrate-like compounds and antigen-like molecules, respectively. There is also described the use of the so prepared enzymes and antibodies.

5 Claims, 4 Drawing Sheets

(1)

(2)

PREPARATION OF SYNTHETIC ENZYMES AND SYNTHETIC ANTIBODIES AND USE OF THE THUS PREPARED ENZYMES AND ANTIBODIES

The present invention is related to a method of preparing synthetic enzymes and synthetic antibodies by using the so called molecular imprinting method. It also concerns the use of thus prepared synthetic enzymes and antibodies.

The array of biochemical reactions found in Nature relies on molecular recognition. This recognition can be found in biological systems such as: antibody-antigen interaction; nucleic acid-histone interaction; lectine-carbohydrate interaction and the interaction between an enzyme and a substrate. In 1894, Emil Fischer proposed the famous "lock and key" model to explain molecular recognition. With this model Fischer could account for how a specific substrate fits into the complementary binding site of an enzyme.

Enzymes perform a key role in biochemical processes, catalyzing the transformation of substrates to products. Structurally the enzymes are, with few exceptions, proteins (polypeptides) of varying size and amino acid residue composition. Each enzyme is designed to catalyze a specific reaction. The high rate and the selectivity of the reaction are two characteristics of an enzyme catalyzed conversion of a substrate to a product.

Industrial as well as research applications of enzymes during this century gave rise to an interest in fully understanding how enzymes function. Together with investigations of enzyme structure and enzymatic reactions, the construction of "synthetic enzymes" (artificial preparations possessing enzymatic behaviour) will prove useful because of the action of these synthetic "enzymes" as catalysts in reaction of industrial interest. In particular synthetic enzymes will prove useful in reactions for which Nature has not developed a natural enzyme.

One of the key features of a natural enzymatic process, apart from the high rate of reaction, is selectivity. The selectivity of enzymes can be divided into the following categories:

a) Enzymes are selective for their substrates. Enzymes can operate in a mixture of compounds, but bind and act upon only one (the substrate) or a few of the components of the mixture.

b) Enzymes are able to direct the chemical reaction to one specific part of the substrate, e.g. an enzyme may catalyze a chemical reaction at one specific site on the substrate while leaving other sites unaffected. These may be equally liable to reaction when performing the reaction by chemical means.

c) Enzymes are selective with respect to the chemical reaction performed. One substrate may undergo a variety of chemical conversions, each catalyzed by a specific enzyme.

d) Enzymes can perform their chemical reactions selectively with respect to the stereostructure of the substrate and product. Only one enantiomeric form of a substrate can be converted, or from a prochiral substrate only one enantiomeric form of the product is produced.

All of these types of selectivity of enzyme catalysis are attractive for the chemist to mimic in the construction of synthetic enzymes. A reaction in the presence of a natural enzyme proceeds at a rate which is several orders of magnitude faster than the non-catalyzed reaction. Furthermore, in nature the substrate is present in a large excess compared to the enzyme, i.e. one enzyme molecule can process several substrate molecules per unit of time ("turn-over").

Different approaches for the preparation of synthetic enzymes have during the years been evaluated. These include the synthesis of compounds based on starting material (cyclodextrin) found in Nature (R. Breslow, A. W. Czarnik, J. Am. Chem. Soc. 105, 1390 (1983)) and the preparation of fully synthetic systems (J-M. Lehn, C. Sirlin, J. Chem. Soc. Chem. Commun., 949, (1978) and D. J. Cram, P. Y. Lam, S. P. Ho, J. Am. Chem. Soc, 108, 839 (1986)).

One aspect of the present invention relates to the use of the molecular imprinting technique in the preparation of synthetic enzymes by the imprinting of "transition state-analogues" and substrate-like compounds.

The other aspect of the present invention relates to the use of the molecular imprinting method in the preparation of synthetic antibodies. In this aspect, in contrast to applying the method in the preparation of synthetic enzymes, only the selective absorbtion of antigens to polymers is considered.

Molecular imprinting (R. Arshady and K. Mosbach, Macromol. Chem., 187, 687 (1981)) is the name given to a process for preparing polymers that are selective for a particular compound (the print molecule). The technique involves: (1) prearranging the print molecule and the monomers and allowing complementary interactions (non-covalent or reversible covalent) to develop: (2) polymerizing around the print molecule-monomer complex; and (3) removing the print molecule from the polymer by extraction (FIG. 1) Polymerization thus preserves the complementarity to the print molecule and the polymer will selectively adsorb the print molecule subsequently. The print molecule binds more favourably to the extracted polymer than do structural analoques. The technique has also been referred to as "host-guest" polymerization or template polymerization.

The so called transition state is formed during an enzymatic conversion of a substrate to a product. The transition state is, in contrast to transition state analogues, extremely unstable. By applying transition state analoques as print-molecules in a molecular imprinting system, the resulting polymer will possess cavities which are complementary to the transition state analogue and therefore in analogy with natural enzymes, bind this compound and accelerate the reaction.

Example 1 relates the preparation of a polymer with hydrolytic properties by the imprinting of a transition state analogue.

This application of transition state analogues is not unlike the isolation of antibodies, raised against a transition state analogue, which possess catalytic activity (so called abzymes) (A. Tramontano, K. Janda, R. Lerner, Science, 234, 1566–1570 (1986) and S. Pollack, J. Jacobs, P. Schultz, Science, 234, 1570–1573, 1986)).

By employing compounds, which resemble the substrate of a reaction, as print molecules in molecular imprinting, one can also prepare polymers which catalyze the reaction. Example 2 relates the preparation of a polymer which accelerate a pyridoxal-dependent enzymatic racemisation. Further instead of using transition state analogues other substrate-like compounds can be used as print molecules leading to polymers possessing enzymatic activity. Thus a compound is chosen, as print molecule in a molecular imprinting procedure, on the basis of which catalytic groups it is able to orientate in the correct spacial position in the site of the polymer where the reaction takes place. After removal of the print molecule, the polymer is incubated with another compound, selected on grounds of its suseptibility to undergo chemical conversion by the positioned catalytic groups in the polymer. This would be analogous to the generation of antibodies containing a site with carboxylate group within bonding distance of an abstractable proton by using the appropriate positively charged hapten. (K. M. Shokat, C. J. Leumann, R. Sugasawara and P. G. Schultz, Nature, 338, 269-271 (1989)).

In another aspect the present invention relates to the use of molecularly imprinted polymers in immunological applications. In this aspect the invention only deals with the selective absorption of antigens to the polymers. In this context different antigens can be employed as print molecules leading to specifically adsorbing polymers ("synthetic antibodies"). Antigens such as smaller molecules (e.g. dopamines, $\gamma$-aminobutyric acid, thyroxines) or more complex structures (e.g. peptides, proteins, glykoproteins) can be employed.

These antigen-selective polymers can directly be applied, in for example heterogenous immunoassays, since they are easily separated from an incubation mixture by filtration or sedimentation. If the imprinted polymers are of a lower molecular weight, these can be applied in a homogenous immunoassay.

For example polymers imprinted with $\gamma$-aminobutyric acid can be used analogous to antibodies (available from Sigma Co., St. Louis) raised against this antigen in an immunoassay.

In summary, the present invention deals with the preparation and the use of molecularily imprinted polymers analogous to natural enzymes and antibodies. Having this in mind, the molecular imprinting technique can be seen as a way of mimicking Nature, with in particular the differences that the polymers are much more stable than the corresponding natural products (proteins/glykoproteins) and that it is possible to prepare catalysts for new reactions. The increased stability is believed to be of great value in industrial applications of such polymers. Furthermore, the molecular imprinting method should in many cases be a simpler technique for obtaining (synthetic) enzymes and antibodies as compared to the more in itself limited (natural) approach.

EXAMPLE 1

Molecular imprinting of p-nitrophenyl methylphosphonate, a transition state analogue, in poly[4(5)-vinylimidazole) leads to a polymer which hydrolyses p-nitrophenol acetate at an increased rate and which can then be inhibited by addition of the p-nitrophenol methylphosphonate.

As shown in FIG. 2, the print molecule, p-nitrophenol methylphosphonate (1) is structurally similar to the substrate molecule p-nitrophenyl acetate (2), but contains a tetrahedral phosphoryl group in place of the carboxy group. Therefore, as with other phosphonate esters (A. Tramontano, K. Janda and R. Lerner, Science, 234, 1566 (1986)) (1), is expected to serve as a transition state analogue for the hydrolysis of (2). An imprint of (1) in the functionally active polymer poly [4(5)-vinylimidazole] (3) was formed by a modification of a method previously used to create metal binding sites in polymers. Cobalt forms a complex with (3). Spectroscopic data indicate that cobalt also forms a complex with (1) (data not shown). As such, cobalt could be essential for the proper imprinting of (1) and, later, the binding of (2). A solution of cobalt (II) ions (1 mmol) and (1) (1 mmol) in deaerated methanol (2 ml) and a bifunctional cross-linker, 1,4-dibromobutane (2 mmol), was added with vigorous agitation to (3) (20 mmol imidazole units in 20 ml of deaerated methanol). After heating for 5 days at 65° C. (note that polymerisation conditions were not optimised), the resultant solid, blue cross-linked polymer, referred to as the 'print polymer' was air-dried. The print molecule (1) was removed by extensive washing with phosphate buffer (100 mM, pH7) and methanol. As a control, polymers were prepared in the presence of the cobalt but without (1) and are referred to as the 'non-print polymers'.

Imidazole-containing polymers are known to catalyse the general hydrolysis of activated esters (C. Overberger and M. Morimoto, J. Am. Chem. Soc., 93, 3222 (1971)) and, as expected, both the print and non-print polymers catalysed the hydrolysis of (2) (FIG. 3). However, the polymer imprinted with the transition state analogue (1) was 60% more active in hydrolysing the appropriate substrate (2) than was the non-print, control polymer. In order to show that this rate enhancement resulted from the molecular imprinting of (1), the hydrolytic activities of both polymers were determined using (1) as an inhibitor [owing to its higher stability, (1) was not hydrolysed by the polymers; data not shown]. As shown in FIG. 3, as the concentration of (1) in the reaction mixture was increased, the hydrolytic activity of the print polymer towards (2) decreased steadily, while the activity of the non-print control was essentially unaffected.

EXAMPLE 2

Molecular imprinting of the coenzyme-substrate analogue N-pyrodoxyl-L-phenylalanine anilide.

Pyridoxal 5-phosphate is a coenzyme involved in many enzymatic reactions such as $\alpha$-decarboxylation, $\alpha,\beta$-elimination, transamination and racemisation. This example relates to a molecular imprint of N-pyridoxyl-L-phenylalanine anilide, a substrate-like compound to the substrate L-phenylalanine in the enzymatically catalyzed racemisation of this amino acid in the presence of pyridoxal 5-phosphate. The resulting polymer is able to separate the enantiomers of the substrate-like compound and also to accelerate the reaction (racemisation) in question. The structures of related compounds are given in FIG. 4. N-pyridoxyl-L-phenylalanine anilide (5) is a substrate-like compound to the Schiff's base intermediate involved in the reaction mechanism (6).

N-pyridoxyl-L-phenylalanine anilide (1): 1.00 g (4.20 mmol) of L-phenylalanine anilide (prepared as described earlier) (D. J. O'Shannessy, B. Ekberg and K. Mosbach, Anal. Biochem., 177, 144 (1989)), 1.17 g (5.74 mmol) of pyridoxal and 690 mg (2 equiv) of KOH were added to 12 ml of methanol. The suspension was stirred for 45 min at 0° C. Excess NaBH$_4$ (170 mg) was added, and the suspension was stirred for another 45 min at 0° C. The mixture was neutralised with acetic acid and the product extracted with chloroform. The product was purified on silica using a gradient of 50-0% heptane in THF as eluent, and crystallized from 60% ethanol. Yield: 1.30 g (79.2%); m.p. 95°-96° C.; $[\alpha]_D^{25} = -17.4°$ (conc.: 9.8 g dm$^{-3}$; in methanol).

$C_{23}H_{25}N_3O_3H_2O$ (409.5) Calc; C 67.46, H 6.65; N 10.26, O 15.63, Found; C 67.2, H 6.71, N 10.2, O 15.8.

$^1$H NMR (CD$_3$OD): $\delta=2.32$ (s; 2'-H), 2.94 (q; $\beta$-H), 3.04 (q; $\beta^1$-H) 3.52 (q: $\alpha$-H), 3.95-4.14 (q; 4'-H), 4.49 (s;

5'-H), 7.13 (m; p-H on anilide), 7.20–7.32 (m; phenyl-H and m-H on anilide), 7.45 (m; o-H on anilide), 7.78 (s; 6-H). Rel. intensities: 3:1:1:1:2:2:1:7:2:1.

MS: m/z 392 ($M^+ + H$; 1%), 300($M^+ + H$, $-C_7H_7$, 3%), 282 ($M^+ + H$, $-C_7H_7$, $-H_2O$, 2%), 271 ($M^+ + H$, $-C_7H_6NO$, 10%), 253 ($M^+ + H$, $-C_7H_8NO_2$, 10%), 120 ($C_7H_6NO$, 100%).

N-Pyridoxyl-D-phenylalanine anilide: This was synthesized in a similar manner. Yield: 82.3%; m.p. 94°–95° C.; $[\alpha]_D^{25} = +18.5°$ (con.: 10.3 g $dm^{-3}$; in methanol).

L-2,3-$^3$H-Phenylalanine anilide: 48 mg (0,29 mmol) of L-phenylalanine containing L-2,3-$^3$H-phenylalanine (obtained from NEN) was reacted with 76 mg (0.35 mmol) of di-tert-butyl dicarbonate in 2 ml of 1,4-dioxane/water (vol. ratio 1:1) for 16 h at pH 9. After work up the Boc-L-phenylalanine was condensed with aniline using 72 mg (0.35 mmol) of dicyclohexylcarbodiimide, 45 mg (0.35 mmol) of N-hydroxybenzotriazole and 60 mg 0.60 mg (0.60 mmol) of aniline in 2 ml of THF overnight. The Boc-group was then removed by treatment with trifluoroacetic acid in methylene chloride, and the product was purified on silica with ethyl acetate as eluent. The compound was identical with authentic L-pheylalanine anilide (D. J. O'Shannessy, B. Ekberg and K. Mosbach Anal. Biochem. 177, 144 (1989)), and had a specific radioactivity of 720, 000 dpm/mol. Yield: 54 mg (77%).

Polymer preparation: The polymers were prepared as described D. J. O'Shannessy, B. Ekberg and K. Mosbach Anal. Biochem. 177, 144 (1989) and D. J. O'Shannessy, B. Ekberg, L. I. Andersson and K. Mosbach J. Chrom. 470, 391 (1989)) with ethylene dimethracrylate as crosslinker and either methacrylic acid of methyl methacrylate as functional monomer. The mole ratio crosslinker/monomer/print molecule was 30:6:1. Polymerization was initiated by 2,2'-azoisobutyronitrile (AIBN) and UV-light at 0° C., and the resulting bulk polymer was ground and sieved to particles of less than 25 um.

Chromatography: A 10 cm × 4.5 mm (i.d.) column was packed as previously described (D. J. O'Shannessy, B. Ekberg and K. Mosbach Anal. Biochem. 177, 144 (1989) and D. J. O'Shannessy, B. Ekberg, L. I. Andersson and K. Mosbach J. Chrom. 470, 391 (1989)) and was run isocratically with 2% acetic acid and 4% chloroform in acetonitrile as eluent.

Incubation procedure: 100 ul of a solution of 10 mmol/L of L-2,3-$^3$H-phenylalanine anilide and 10 mmol/L of pyridoxal (free base) in acetonitrile containing 2% acetic acid and 4% chloroform was incubated with 20 mg of polymer particles for 24 h at ambient temperature. The reaction mixture was distributed between 1000 ul of chloroform and 500 ul of 10% $K_2CO_3$, and 400 ul of the upper aqueous layer was counted by liquid scintillation.

A polymer prepared in the presence of N-pyridoxyl-L-phenylalanine anilide could be run in a HPLC-mode (chromatography above) to efficiently separate (separation factor 2,5) the two enantiomers of the print molecule (N-pyridoxyl-L-phenylalanine anilide. Furthermore, a substrate selectivity was also demonstrated in that N-pyridoxyl-L-phenylalanine anilide was the compound retained in highest extent on a column in comparison to N-pyridoxyliden-phenylalanine anilide, phenylalanine anilide, pyridoxal and pyridoxamine.

A polymer material prepared in the presence of N-pyridoxyl-L-phenylalanine anilide exhibited, in the above described incubation procedure, a ninefold higher efficiency in racemizing L-phenylalanine anilide than a polymer prepared in the absence of N-pyridoxyl-L-phenylalanine anilide.

BRIEF DESCRIPTION OF THE DRAWINGS

FIGS. 4-1, 4-2, 4-3, 4-4, 4-5 and 4-6 describes structures of related compounds.

LEGENDS TO FIGURES

Figure 1:
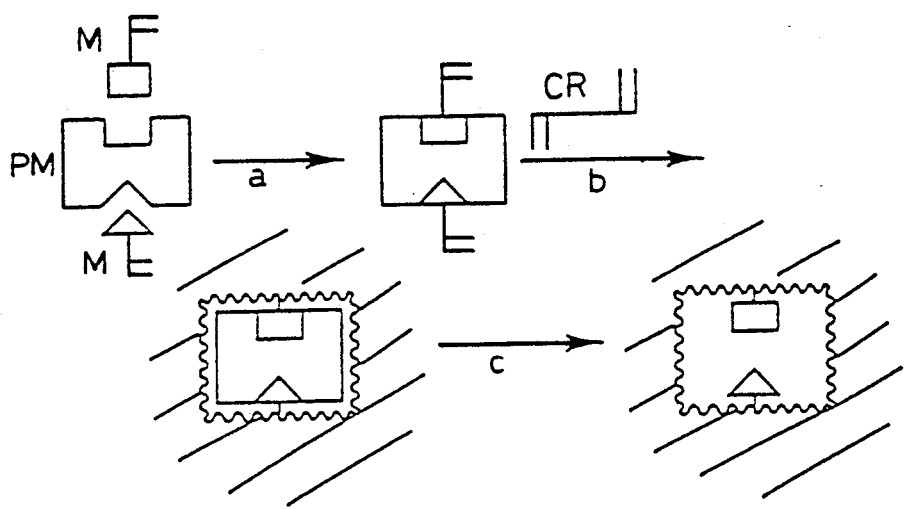
FIG. 1 illustrates a molecular imprinting process.

FIG. 1. The principle of molecular imprinting. Development of complementary interactions between the print molecule and the monomers (a); polymerization (b); removal of the print molecule from the polymer (c) M, monomers; PM, print molecule; CR, crosslinker.

Figure 2:
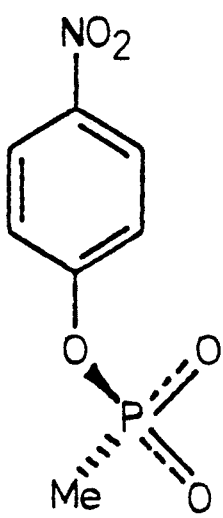
FIG. 2 shows the chemical structure of a print molecule.
Figure 2:
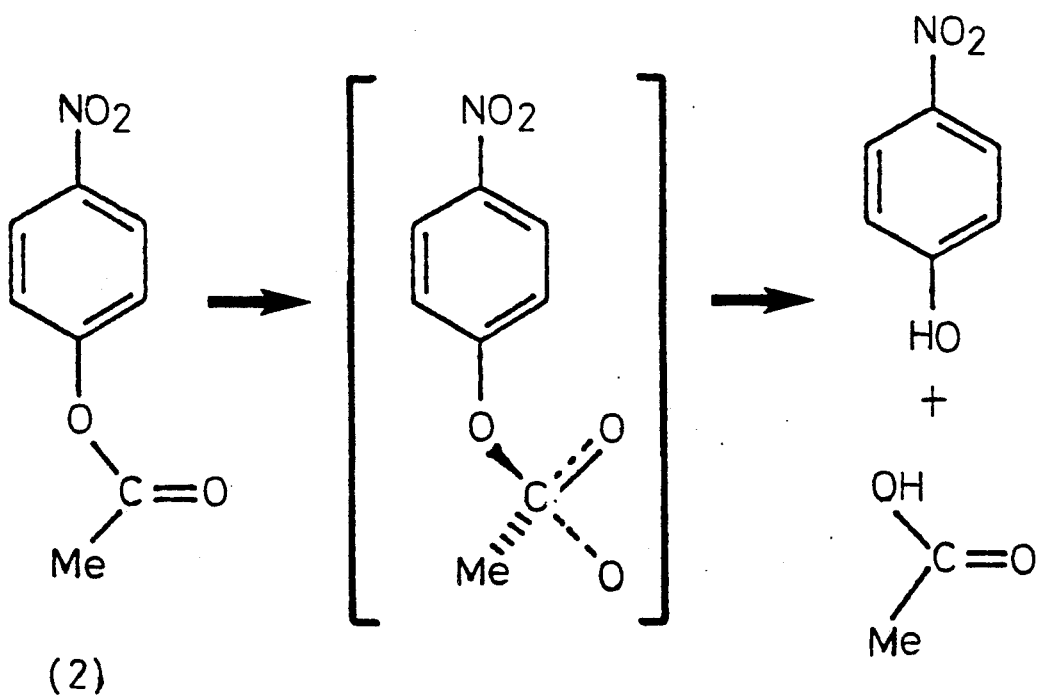

FIG. 2; (1), p-nitrophenyl methylphosphonate; serves as a transition state analogue for the hydrolysis of p-nitrophenyl acetate (2).

Figure 3:
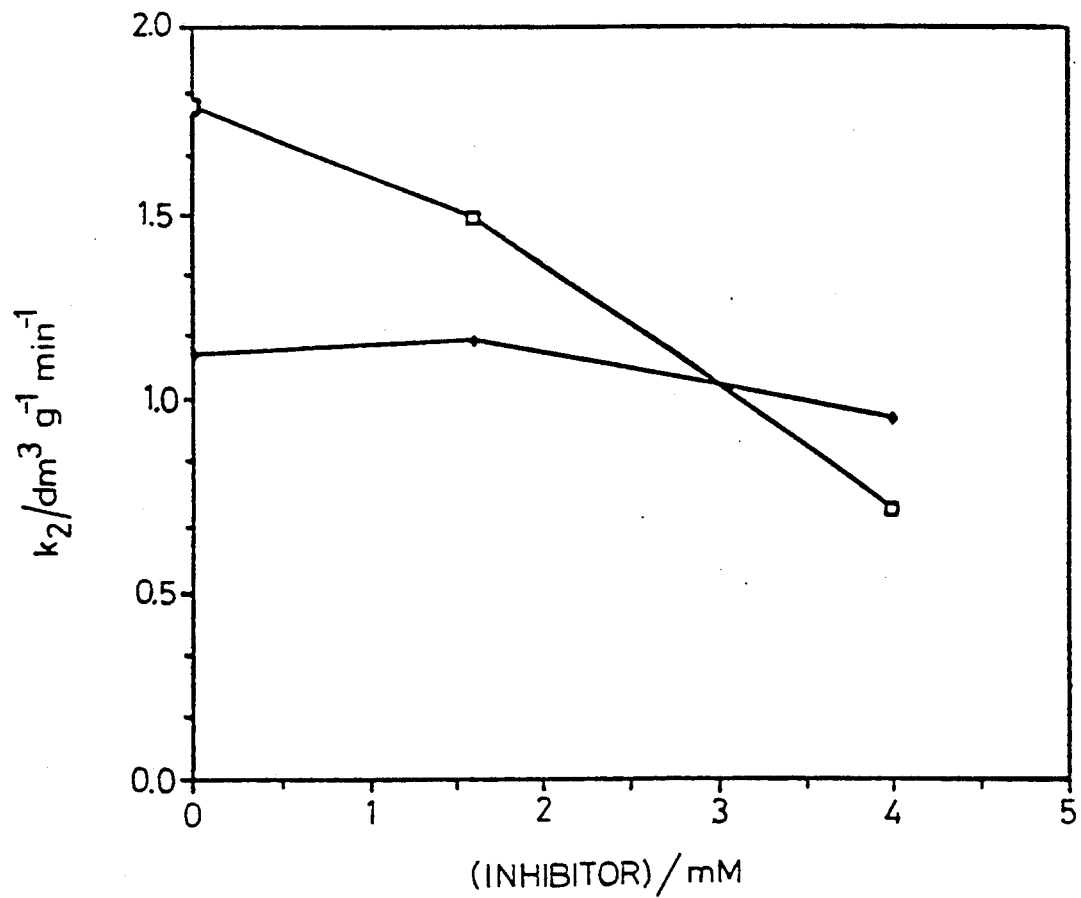
FIG. 3 is a graph which shows the relationship between hydrolytic activity and amount of inhibitor.

FIG. 3. Inhibition of the hydrolysis of (2) by addition of the transition state analogue used as the print molecule: second-order rate constant vs. inhibitor concentration. The rate of hydrolysis of p-nitrophenol acetate by the non-print control polymer (■) and the polymer imprinted with the transition state analo-gue (1) (□) was measured using (1) as an inhibitor. The hydrolysis of (2) was monitored as an increase in absorbance at 400 nm. Print and non-print polymers were suspended in 10% methanol: Tris, 0.05M, pH 8.0, 0.5M NaCl buffer at 25° C. Kinetic constants are based on a dry polymer concentration of 2 g $l^{-1}$.

Figures 1, 4:
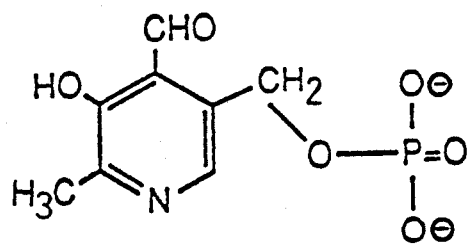
Figures 2, 4:
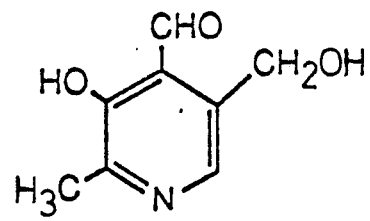
Figures 3, 4:
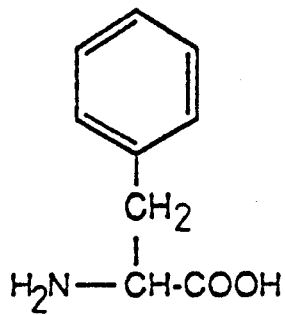
Figure 4:
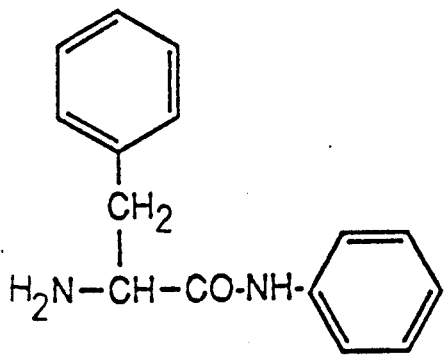
Figures 4, 5:
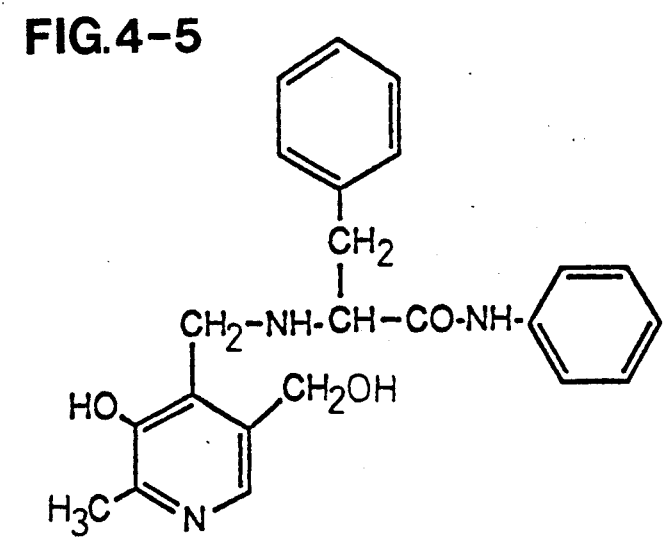
Figures 4, 5, 6:
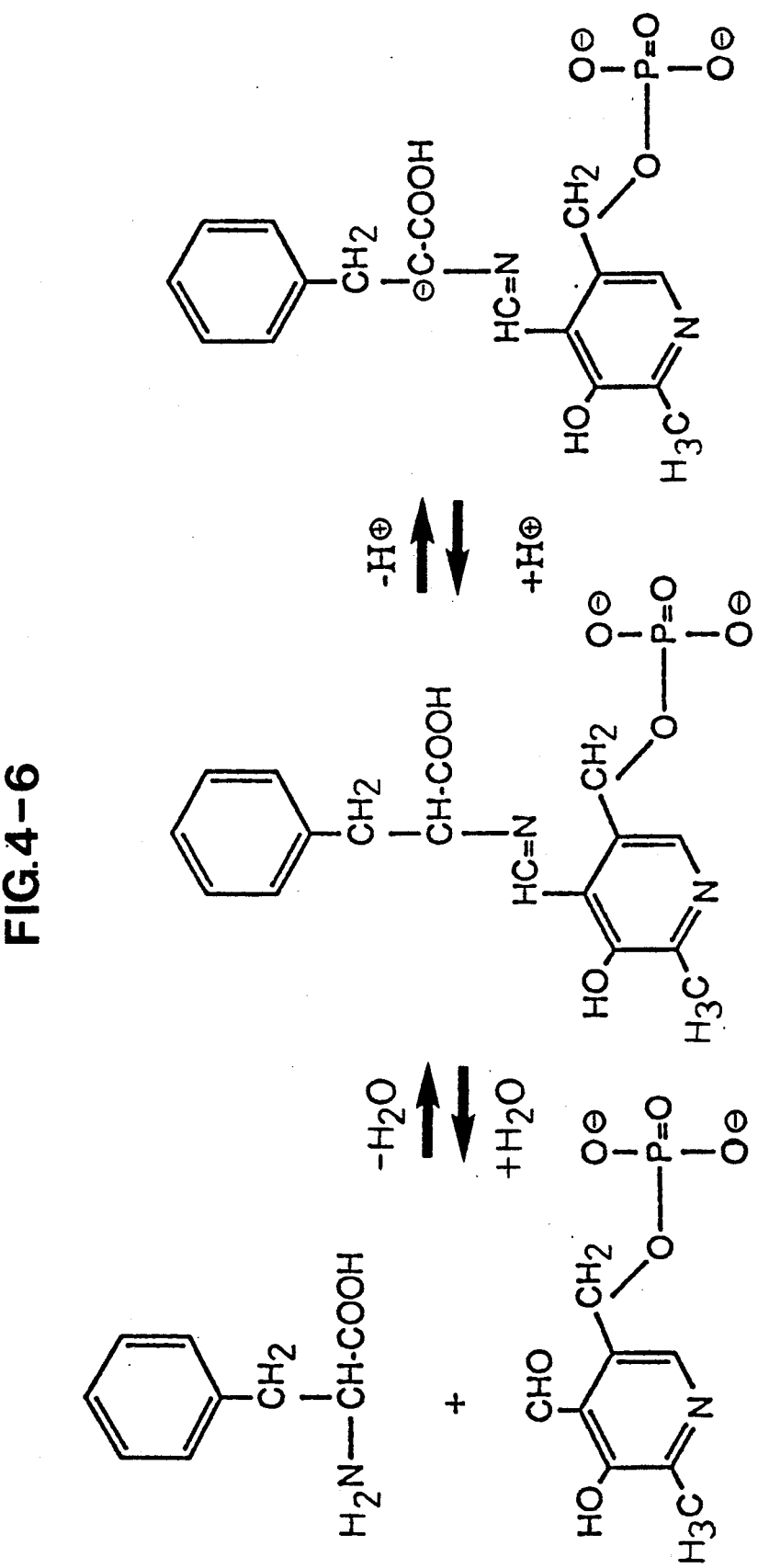

FIG. 4. (1), pyridoxalphosphate; (2), pyridoxal; (3), L-phenylalanine; (4), L-phenylalanine anilide; (5), N-pyridoxyl-L-phenylalanine anilide; (6), the mechanism for racemisation of L-phenylalanine in the presence of pyridoxalphosphate. The rate of racemisation of L-phenylalanine anilide can be followed experimentally by measuring the α-protonexchange of L-phenylalanine anilide labelled with tritium at this position.

I claim:

1. A method of producing synthetic enzymes or synthetic antibodies, comprising the orientation of monomers around a print molecule, addition of crosslinkers, polymerizing to a polymer and subsequent removal of the print molecule, thereby creating a cavity in the polymer corresponding to said print molecule.

2. A method of producing synthetic enzymes, comprising polymerisation of monomers to a polymer around a print molecule and thereafter removing the print molecule, thereby creating a cavity in the polymer corresponding to said print molecule.

3. A method according to claim 1 or 2 for producing enzymes, whereby as print molecule use is made of a transition state analogue.

4. A method according to claim 1 or 2 for producing enzymes, whereby as print molecule use is made of a substrate-like compound.

5. A method according to claim 1 for producing synthetic antibodies, whereby as print molecule use is made of an antigen-like compound.

* * * * *